(12) United States Patent
Hwang et al.

(10) Patent No.: US 10,281,419 B2
(45) Date of Patent: May 7, 2019

(54) HYDROGEL-BASED INTERDIGITATED MICROELECTRODE BIOSENSOR

(71) Applicant: KOREA INSTITUTE OF SCIENCE AND TECHNOLOGY, Seoul (KR)

(72) Inventors: Kyoseon Hwang, Seoul (KR); Nakwon Choi, Seoul (KR); Jinsik Kim, Seoul (KR); Hye Jin Kim, Seoul (KR); Yong Kyoung Yoo, Seoul (KR); Sang Yun Yeom, Seoul (KR); Woongsun Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/105,740

(22) PCT Filed: Mar. 29, 2016

(86) PCT No.: PCT/KR2016/003195
§ 371 (c)(1),
(2) Date: Jun. 17, 2016

(87) PCT Pub. No.: WO2017/090838
PCT Pub. Date: Jun. 1, 2017

(65) Prior Publication Data
US 2017/0227482 A1    Aug. 10, 2017

Related U.S. Application Data

(63) Continuation of application No. PCT/KR2016/003195, filed on Mar. 29, 2016.

(30) Foreign Application Priority Data

Nov. 24, 2015 (KR) .......................... 10-2015-0164513

(51) Int. Cl.
*G01N 27/12* (2006.01)
*G01N 33/53* (2006.01)
(Continued)

(52) U.S. Cl.
CPC ........... *G01N 27/125* (2013.01); *G01N 27/12* (2013.01); *G01N 27/128* (2013.01);
(Continued)

(58) Field of Classification Search
CPC ............... G01N 27/125; G01N 27/128; G01N 33/48707; G01N 33/54306; G01N 33/5438
See application file for complete search history.

(56) References Cited

U.S. PATENT DOCUMENTS

2006/0024813 A1*  2/2006  Warthoe ................ B82Y 15/00
                                                  435/287.1
2009/0159445 A1*  6/2009  Krishna ................ G01N 27/125
                                                  204/424

FOREIGN PATENT DOCUMENTS

KR    1020070085460 A    8/2007
KR    10-0777973 B1      11/2007

OTHER PUBLICATIONS

Al-Ameen, Mohammad Ali, and Gargi Ghosh. "Sensitive quantification of vascular endothelial growth factor (VEGF) using porosity induced hydrogel microspheres." Biosensors and Bioelectronics 49 (2013): 105-110.*

* cited by examiner

*Primary Examiner* — Robert J Eom
(74) *Attorney, Agent, or Firm* — Goldilocks Zone IP Law (57) ABSTRACT

A hydrogel-based interdigitated microelectrode biosensor is disclosed. The hydrogel-based interdigitated microelectrode biosensor includes: a first interdigitated microelectrode having a plurality of first protrusion electrodes arranged in a
(Continued)

comb-like shape on a substrate; a second interdigitated microelectrode facing the first interdigitated microelectrode and having a plurality of second protrusion electrodes arranged in a comb-like shape on the substrate, the second protrusion electrodes being arranged alternately with the first protrusion electrodes of the first interdigitated microelectrode; and a hydrogel filled in a space between the first and second interdigitated microelectrodes arranged alternately with each other. The hydrogel is provided between the interdigitated microelectrodes such that the presence and concentration of a biological substance, such as a protein, are detected by measuring the impedance between the interdigitated microelectrodes.

4 Claims, 10 Drawing Sheets

(51) Int. Cl.
     *G01N 33/483*      (2006.01)
     *G01N 33/487*      (2006.01)
     *G01N 33/543*      (2006.01)
(52) U.S. Cl.
     CPC ..... *G01N 33/483* (2013.01); *G01N 33/48707* (2013.01); *G01N 33/53* (2013.01); *G01N 33/5438* (2013.01); *G01N 33/54306* (2013.01)

(a) Antibodies are three-dimensionally bindable to hydrogel (b) Taget substance is sortable according to its size

HYDROGEL-BASED INTERDIGITATED MICROELECTRODE BIOSENSOR

CROSS REFERENCE TO RELATED PATENT APPLICATIONS

This application claims the benefit under 35 U.S.C. Section 371, of PCT International Application No. PCT/KR2016/003195, filed Mar. 29, 2016, which claimed priority to Korean Patent Application No. 10-2015-0164513, filed Nov. 24, 2015, the disclosures of which are hereby incorporated by the references.

BACKGROUND OF THE INVENTION

1. Field of the Invention

The present invention relates to an interdigitated microelectrode biosensor, and more specifically to a hydrogel-based interdigitated microelectrode biosensor in which a hydrogel is provided between interdigitated microelectrodes such that the presence and concentration of a biological substance, particularly a protein, are detected by measuring the impedance between the interdigitated microelectrodes, achieving increased impedance detection width and limit by tens to hundreds of times and improved impedance detection accuracy compared to conventional interdigitated microelectrode sensors.

2. Description of the Related Art

In recent years, many biosensors have been developed for detecting the presence and concentration of a variety of biological substances, such as genes and proteins, by electrical methods. One example is to use interdigitated microelectrodes. Since biosensors using interdigitated microelectrodes have a very substantially broad region in a zigzag configuration where receptors capable of specific binding to a biological substance are immobilized, they are praised for their ability to measure even a low concentration of the biological substance.

Such a biosensor using interdigitated microelectrodes is disclosed in Korean Patent No. 777973 (published on Nov. 29, 2007). According to this patent, since the concentration of a biological substance is measured based on an electric current flowing between the electrodes, it is necessary to use conductive particles for the flow of electric current between the electrodes. However, the use of the conductive particles is troublesome.

The biosensor has the problem that a larger amount of an electric field having an influence on the impedance between the electrodes escapes upward from the electrodes than the amount generated between the electrodes. That is to say, the impedance variation is more affected by changes generated above the electrodes than by reactions generated between the electrodes. As a result, a narrow width and a low limit of impedance detection as well as a low accuracy of impedance detection are obtained, implying poor reliability and availability of the sensor.

SUMMARY OF THE INVENTION

The present invention has been made in an effort to solve the above problems, and it is an object of the present invention to provide a hydrogel-based interdigitated microelectrode biosensor in which a hydrogel is provided between interdigitated microelectrodes such that the presence and concentration of a biological substance, such as a protein, are detected by measuring the impedance between the interdigitated microelectrodes, achieving increased impedance detection width and limit by tens to hundreds of times and improved impedance detection accuracy compared to conventional interdigitated microelectrode sensors.

According to an embodiment of the present invention, a hydrogel-based interdigitated microelectrode biosensor includes: a first interdigitated microelectrode having a plurality of first protrusion electrodes arranged in a comb-like shape on a substrate; a second interdigitated microelectrode facing the first interdigitated microelectrode and having a plurality of second protrusion electrodes arranged in a comb-like shape on the substrate, the second protrusion electrodes being arranged alternately with the first protrusion electrodes of the first interdigitated microelectrode; and a hydrogel filled in a space between the first and second interdigitated microelectrodes arranged alternately with each other.

In the hydrogel-based interdigitated microelectrode biosensor of the present invention, the hydrogel is provided between the interdigitated microelectrodes such that the presence and concentration of a biological substance, such as a protein, are detected by measuring the impedance between the interdigitated microelectrodes. This construction is effective in increasing the width and limit of impedance detection by tens to hundreds of times and improving the accuracy of impedance detection compared to conventional interdigitated microelectrode sensors.

In addition, the presence of size-controllable pores in the hydrogel allows the detection of increased amounts of biological substances with high efficiency. This leads to an improvement in impedance detection limit, ensuring enhanced reliability and availability of the hydrogel-based interdigitated microelectrode biosensor.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Embodiments of the present invention will now be described in more detail with reference to the accompanying drawings.

Figure 1:
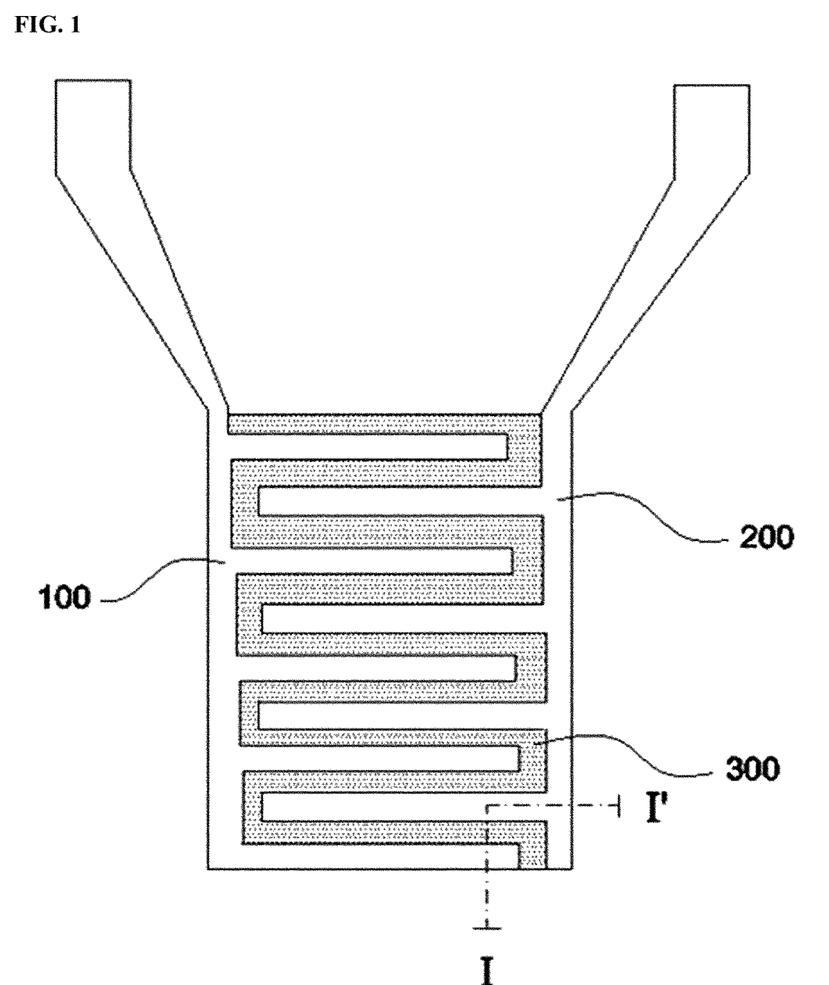
FIG. 1 illustrates the construction of a hydrogel-based interdigitated microelectrode biosensor according to an embodiment of the present invention.
Figure 2:
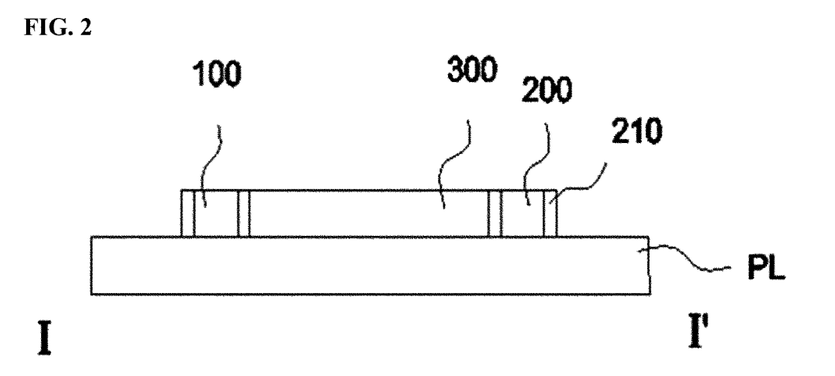
FIG. 2 is a cross-sectional view of a region taken along line I-I' of FIG. 1.

FIG. 1 illustrates the construction of a hydrogel-based interdigitated microelectrode biosensor according to an embodiment of the present invention and FIG. 2 is a cross-sectional view of a region taken along line I-I' of FIG. 1.

Figure 3:
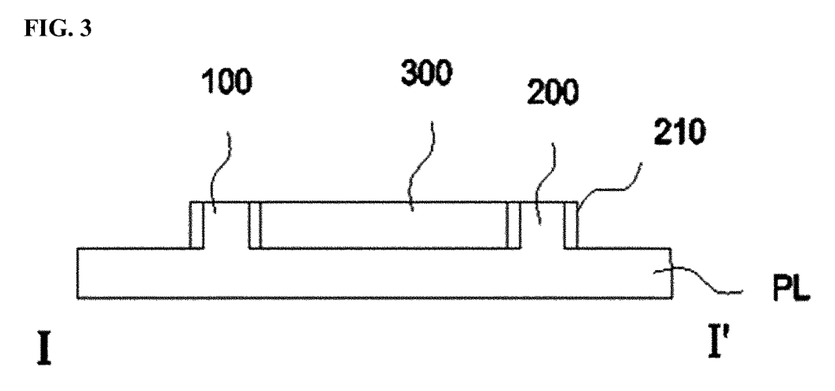
FIG. 3 is another cross-sectional view of a region taken along line I-I' of FIG. 1.

As illustrated in FIGS. 1 to 3, the hydrogel-based interdigitated microelectrode biosensor includes: a first interdigitated microelectrode 100 having a plurality of first protrusion electrodes arranged in a comb-like shape on a substrate PL; a second interdigitated microelectrode 200 facing the first interdigitated microelectrode 100 and having a plurality of second protrusion electrodes arranged in a comb-like shape on the substrate PL, the second protrusion electrodes being arranged alternately with the first protrusion electrodes of the first interdigitated microelectrode 100; and a hydrogel 300 filled in a space between the first interdigitated microelectrode and the second interdigitated microelectrode 200 arranged alternately with each other.

First, the detection of impedance using the hydrogel-based interdigitated microelectrode biosensor will be explained. The impedance between the first interdigitated microelectrode 100 and the second interdigitated microelectrode 200 is summarized as follows:

$$Z = R + jX$$
$$= R + j(XL - XC)$$
$$= R - jXC$$
$$= R - j(1/wC)$$

where Z is impedance, R is resistance, X is reactance, C is capacitance, and w is angular frequency. The reactance X is divided into inductor component XL and capacitor component XC. The inductor component XL is ignored and only the capacitor component XC remains because the first interdigitated microelectrode 100 is not directly connected to the second interdigitated microelectrode 200.

Thus, when a target biological substance responds specifically to receptors (mainly antibodies, aptamers, etc.) immobilized on the hydrogel 300 filled in a space between the first interdigitated microelectrode 100 and the second interdigitated microelectrode 200, an impedance variation in the space between the first interdigitated microelectrode 100 and the second interdigitated microelectrode 200, i.e. the space where the hydrogel 300 is formed, is measured, from which the target biological substance can be quantitatively analyzed.

As illustrated in each of FIGS. 2 and 3, the formation of the hydrogel 300 in the space between the first interdigitated microelectrode 100 and the second interdigitated microelectrode 200 allows electric field and impedance variations to occur predominantly in the horizontal direction with respect to the direction in which the first interdigitated microelectrode 100, the hydrogel 300, and the second interdigitated microelectrode 200 are arranged in this order. With this arrangement, an electric field and an impedance are prevented from escaping upward from or perpendicularly to the first interdigitated microelectrode 100, the hydrogel 300, and the second interdigitated microelectrode 200. The generation of an electric field and an impedance in the horizontal direction can increase the width of impedance detection by tens to hundreds of times.

Figure 4:
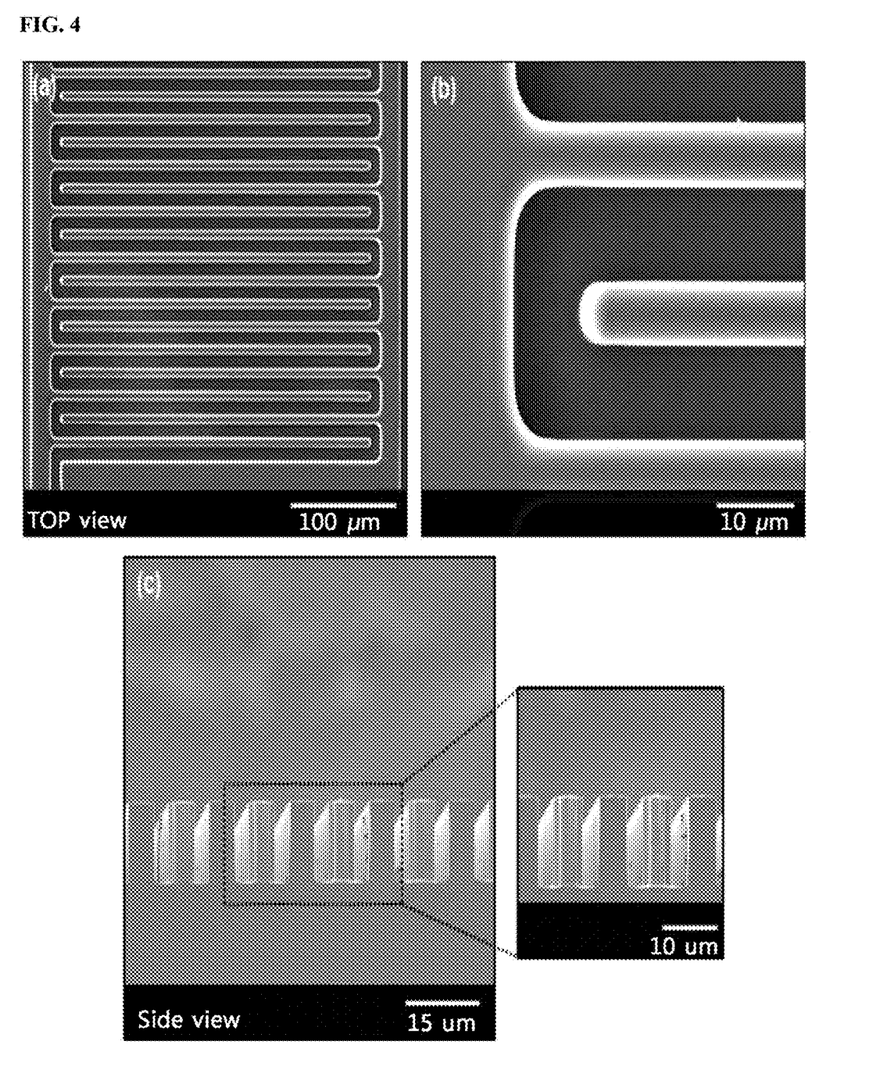
FIG. 4 shows detailed cross-sectional images of actual models of the interdigitated microelectrodes illustrated in FIGS. 1 and 2.

FIG. 3 is another cross-sectional view of a region taken along line I-I' of FIG. 1 and FIG. 4 shows detailed cross-sectional images of actual models of the interdigitated microelectrodes illustrated in FIGS. 1 and 2.

FIG. 3 illustrates the same construction as that of FIG. 2 except that different patterning methods are used to form the first interdigitated microelectrode 100 and the second interdigitated microelectrode 200, each of which is surrounded by a metal pattern 210 at both sides thereof.

Specifically, FIG. 2 exemplifies a construction in which patterns of the first interdigitated microelectrode 100 and the second interdigitated microelectrode 200 are formed in comb-like shapes on a substrate PL by a photolithography process using a photoresist or polymer and a silicon structure and a metal pattern 210 surrounding both sides of each of the patterns of the first interdigitated microelectrode 100 and the second interdigitated microelectrode 200 is formed by a photolithography process.

In contrast, FIG. 3 exemplifies a construction in which a silicon substrate PL is patterned by a photolithography process to form patterns of the first interdigitated microelectrode 100 and the second interdigitated microelectrode 200 in comb-like shapes and a metal pattern 210 surrounding both sides of each of the patterns of the first interdigitated microelectrode 100 and the second interdigitated microelectrode 200 is formed by a photolithography process.

Thereafter, the hydrogel 300 is filled in a space between the first interdigitated microelectrode 100 and the second interdigitated microelectrode 200. An impedance variation in the space where the hydrogel 300 is formed is measured to quantitatively analyze a target biological substance.

Figure 5:
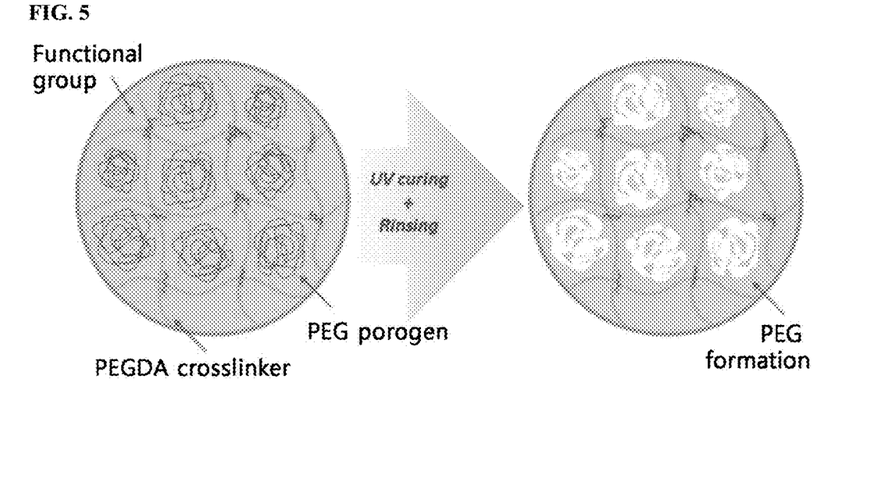
FIG. 5 is a schematic cross-sectional diagram showing the formation of pores in the hydrogel illustrated in FIG. 1.

FIG. 5 is a schematic cross-sectional diagram showing the formation of pores in the hydrogel illustrated in FIG. 1.

Referring to FIG. 5, the hydrogel 300 is a material that has a three-dimensional network structure and is composed of a polyethylene glycol diacrylate (PEGDA) crosslinker, a polyethylene glycol (PEG) porogen, and various functional groups. The PEGDA crosslinker forms a network structure and the PEG porogen determines the size of pores.

When the liquid hydrogel 300 is exposed to UV, the PEGDA crosslinker is activated to form a three-dimensional network structure. Removal of the PEG porogen by subsequent rinsing leaves pores in the three-dimensional network structure.

FIG. 5 shows a change in the cross-section of the hydrogel before and after UV curing and rinsing. When different kinds of PEG porogens are used, pores with different sizes are formed in the hydrogel 300. The functional groups present in the network structure of the hydrogel 300 can three-dimensionally immobilize antigens and various receptors. The size of pores can be controlled depending on the kind of the PEG porogen.

Figure 6:
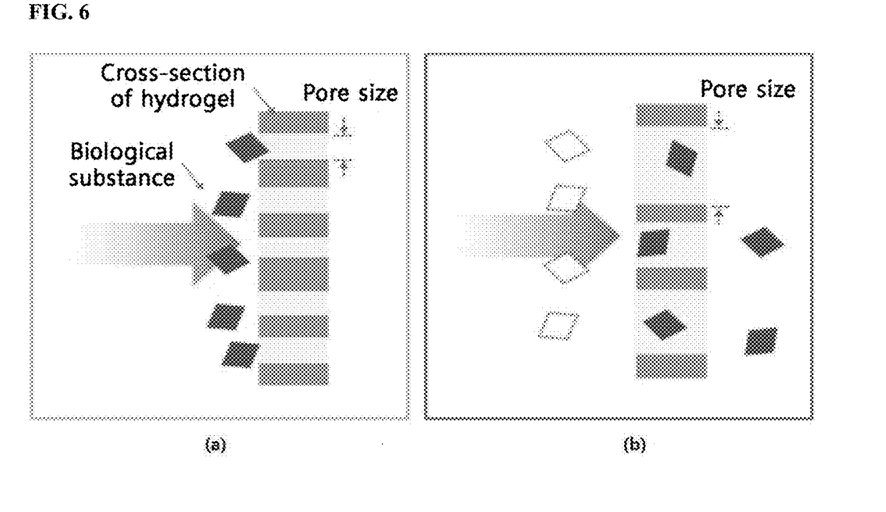
FIG. 6 is a schematic cross-sectional diagram showing a change in the hydrogel illustrated in FIG. 5 with varying pore sizes of the hydrogel.

FIG. 6 shows a schematic cross-sectional diagram showing a change in the hydrogel illustrated in FIG. 5 with varying pore sizes of the hydrogel.

As shown in FIG. 6, when the pore size of the hydrogel 300 is smaller than the size of a biological substance, the biological substance cannot penetrate through the hydrogel 300. In contrast, when the pore size of the hydrogel 300 is larger than the size of a biological substance, the biological substance can pass through the hydrogel 300.

Thus, when a target biological substance responds specifically to receptors in the hydrogel 300 filled and activated in the space between the first interdigitated microelectrode 100 and the second interdigitated microelectrode 200, an impedance variation in the space is measured, from which the target biological substance can be quantitatively analyzed. That is, the use of the hydrogel-based interdigitated microelectrode sensor enables the detection of a biological substance.

Figure 7:
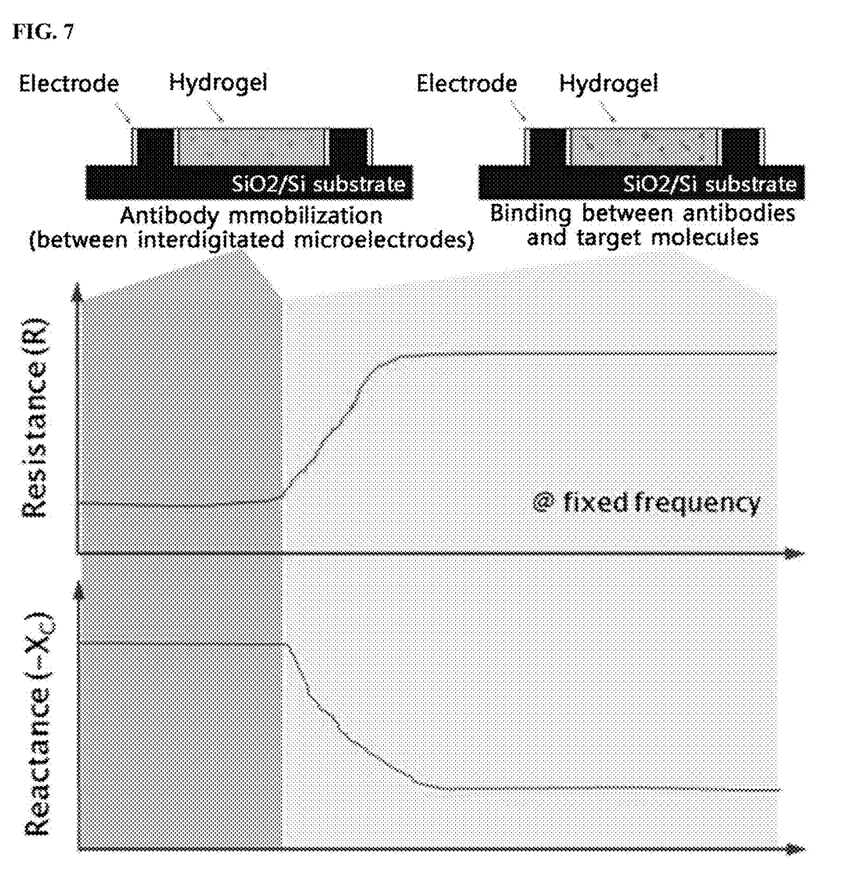
FIG. 7 graphically shows a variation in the impedance of an interdigitated microelectrode biosensor before and after reactions between antibodies and target biomolecules.

FIG. 7 graphically shows a variation in the impedance of the interdigitated microelectrode biosensor before and after reactions between antibodies and target biomolecules.

As shown in FIG. 7, when the antibodies bind specifically to the target biological substance, a variation in resistance occurs between the first interdigitated microelectrode 100 and the second interdigitated microelectrode 200 where the target molecules are located. The capacitance C decreases due to the properties of the target molecules, resulting in an increase in reactance $X_C$ (i.e. a decrease in $-X_C$). The amount of the target molecules can be exactly detected by measuring the resistance and reactance variations.

In the case where a conventional interdigitated microelectrode sensor is used to detect a biological substance, antibodies immobilized between the electrodes are allowed to bind to the target molecules and an impedance variation is observed. In this case, the antibodies are immobilized two-dimensionally on the surface between the electrodes. In contrast, according to an embodiment of the present invention, antibodies can be immobilized three-dimensionally on the network structure of the hydrogel 300 formed between the first interdigitated microelectrode 100 and the second interdigitated microelectrode 200. This two-dimensional immobilization extends the dynamic range of the sensor.

Figure 8:
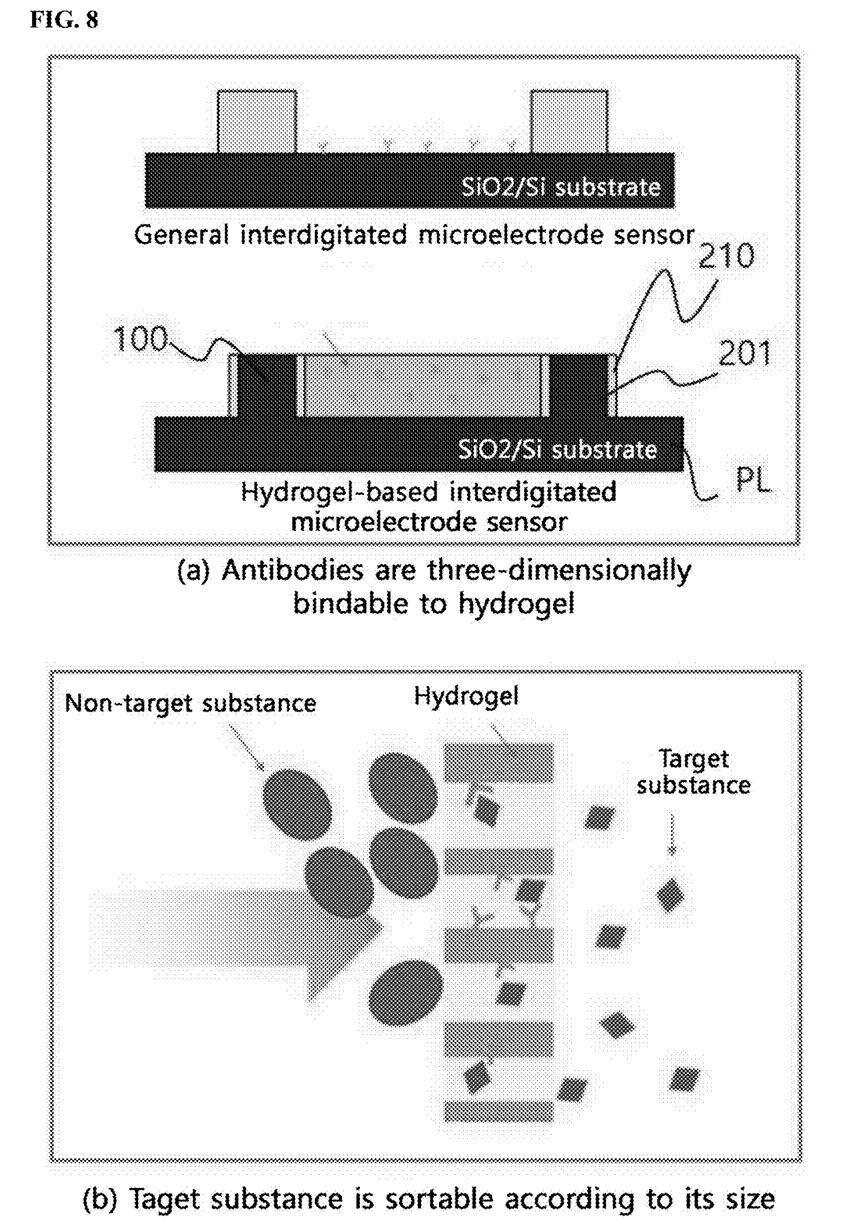
FIG. 8 shows schematic cross-sectional diagrams showing the construction and another feature of the hydrogel-based interdigitated microelectrode biosensor of FIGS. 1 and 2.

FIG. 8 shows schematic cross-sectional diagrams showing the construction and another feature of the hydrogel-based interdigitated microelectrode biosensor of FIGS. 1 and 2.

Referring to FIG. 8, the pores of the hydrogel 300 formed between the first interdigitated microelectrode 100 and the second interdigitated microelectrode 200 are adjusted to a size similar to that of the target substance so that larger non-target substances can be filtered. That is, the pore size of the hydrogel 300 can be adjusted depending on the size of the target substance to sort the target substance.

The pore size of the hydrogel 300 can be controlled by varying the UV curing conditions (including curing time and UV intensity) for the activation of the PEGDA crosslinker to form a three-dimensional network structure.

Figure 9:
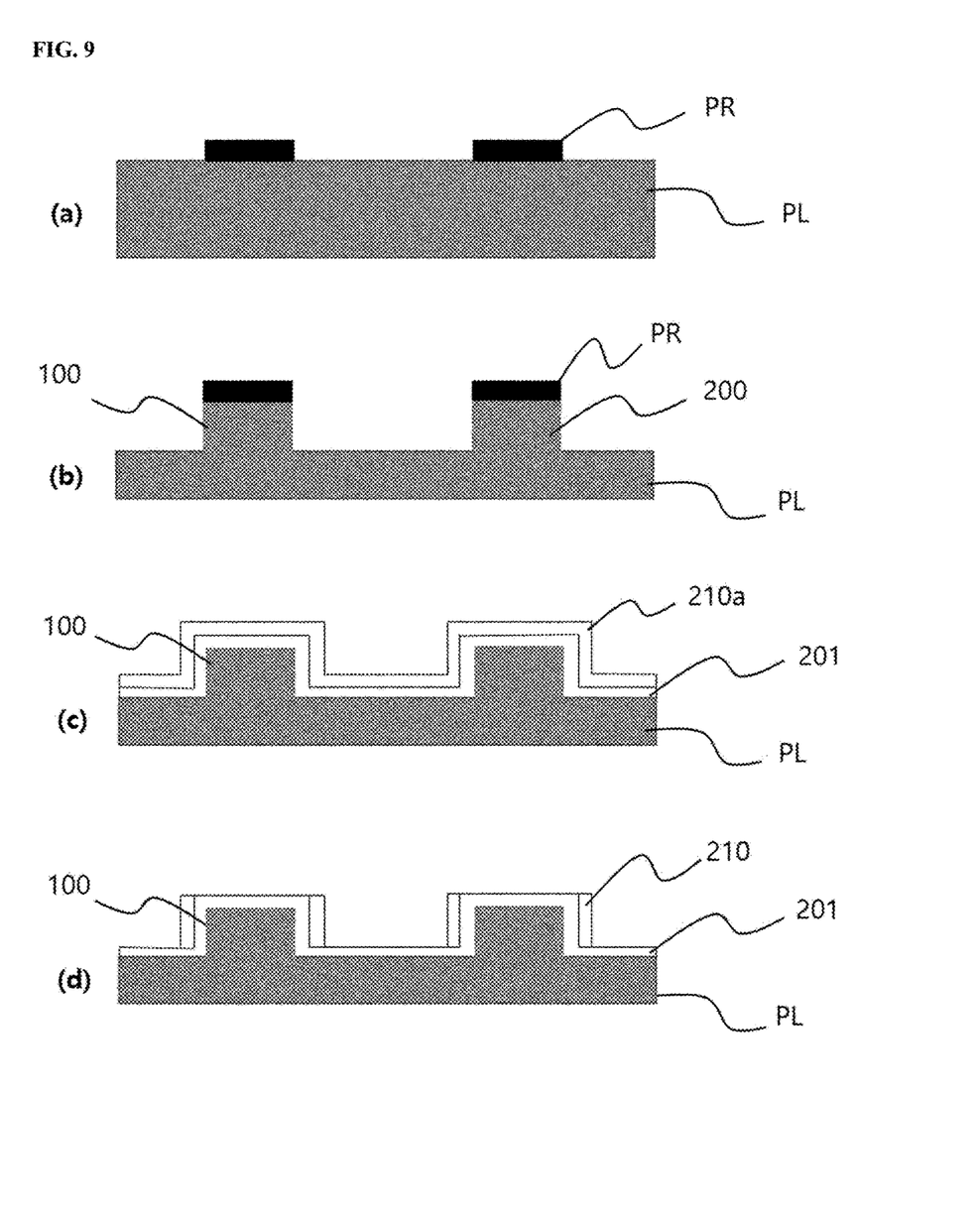
FIG. 9 illustrates cross-sectional views explaining a method for fabricating the interdigitated microelectrode biosensor of FIGS. 1 and 2.

FIG. 9 illustrates cross-sectional views explaining a method for fabricating the interdigitated microelectrode biosensor of FIGS. 1 and 2.

The interdigitated microelectrode biosensor may be fabricated by two approaches based on microelectromechanical system (MEMS) micromachining technology.

The first approach is illustrated in FIG. 9. As illustrated in FIG. 9, patterns of the first interdigitated microelectrode 100 and the second interdigitated microelectrode 200 are formed in comb-like shapes on a silicon substrate PL by a photolithography process and a metal pattern 210 surrounding both sides of each of the patterns of the first interdigitated microelectrode 100 and the second interdigitated microelectrode 200 is formed by a photolithography process.

Specifically, a photoresist (PR) is patterned on a silicon substrate PL ((a) FIG. 9) and the silicon substrate PL is etched by a photolithography process using deep reactive ion etching (DRIE) to form first and second interdigitated microelectrode patterns in comb-like shapes ((b) of FIG. 9).

Next, a 300 nm thick silicon oxide ($SiO_2$) film is deposited on the entire surface of the substrate PL, including the first and second interdigitated microelectrode patterns, by plasma enhanced chemical vapor deposition (PECVD) to form an insulating layer 201 ((c) of FIG. 9).

Subsequently, titanium (Ti) and platinum (Pt) are sequentially deposited to thicknesses of 50 nm and 200 nm on the insulating layer 201 by sputtering, respectively ((d) of FIG. 9). The Ti layer and the Pt layer can be used as adhesion layers to increase the bonding strength of the silicon dioxide layer. The Pt layer and the Ti layer of the silicon structure, in which $SiO_2$/Ti/Pt are deposited in this order, are etched with an inductively coupled plasma reactive ion etcher (ICP-RIE). As a result of this etching, microelectrodes can be formed from the metal patterns 210.

Figure 10:
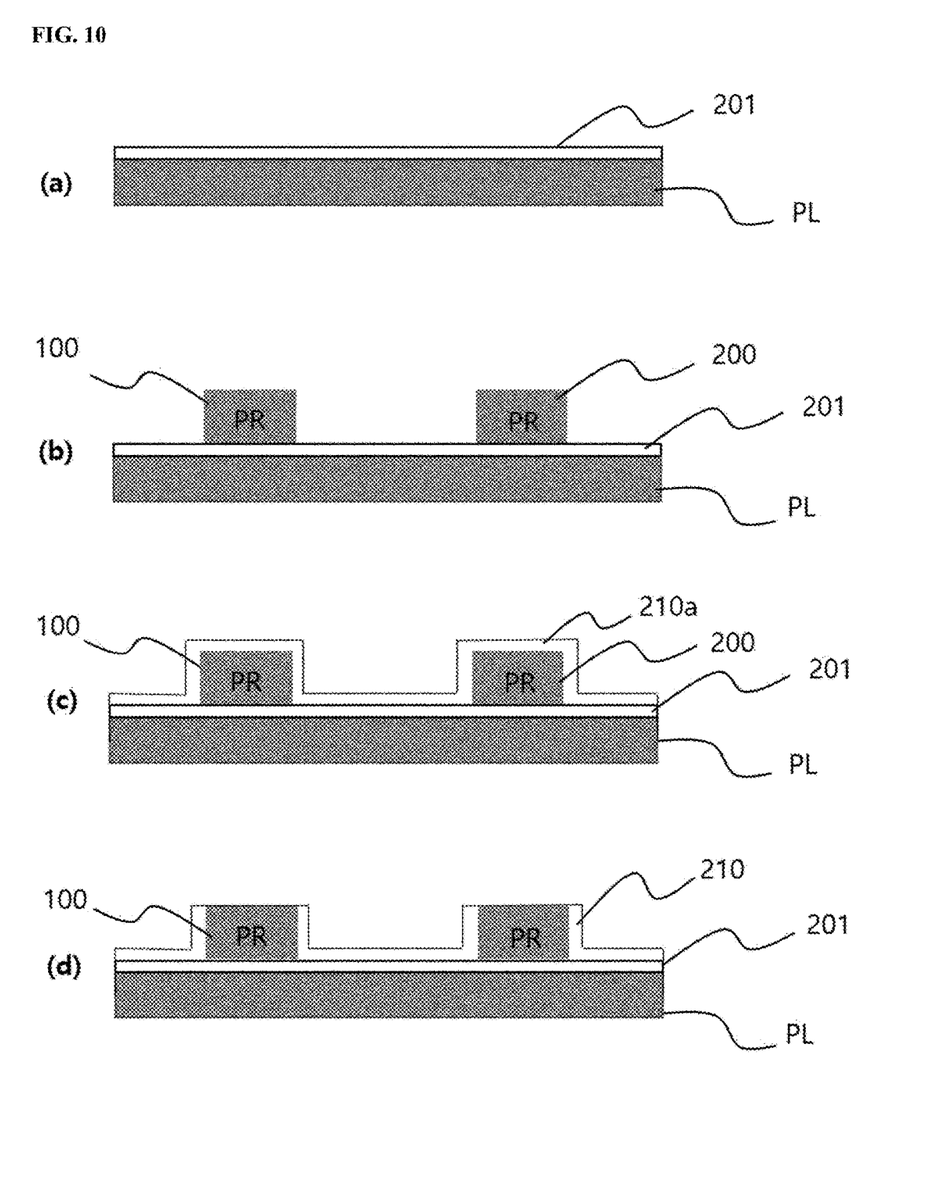
FIG. 10 illustrates cross-sectional views explaining a method for fabricating the interdigitated microelectrode biosensor of FIGS. 1 and 3.

FIG. 10 illustrates cross-sectional views explaining a method for fabricating the interdigitated microelectrode biosensor of FIGS. 1 and 3.

As illustrated in FIG. 10, patterns of the first interdigitated microelectrode 100 and the second interdigitated microelectrode 200 are formed in comb-like shapes on a substrate PL by a photolithography process using a photoresist or polymer and a silicon structure and a metal pattern 210 surrounding both sides of each of the patterns of the first and second interdigitated microelectrodes are formed by a photolithography process.

Specifically, a 300 nm thick silicon oxide film is deposited on a silicon substrate PL by PECVD to form an insulating layer 201 ((a) of FIG. 10).

Then, a photoresist (PR) is micropatterned to form patterns of first and second interdigitated microelectrodes ((b) of FIG. 10).

Titanium (Ti) and platinum (Pt) are sequentially deposited to thicknesses of 50 nm and 200 nm by sputtering, respectively ((c) of FIG. 10), and the Pt layer and the Ti layer are sequentially etched by ICP-RIE. As a result of this etching, microelectrodes can be formed from the metal patterns 210.

Figure 11:
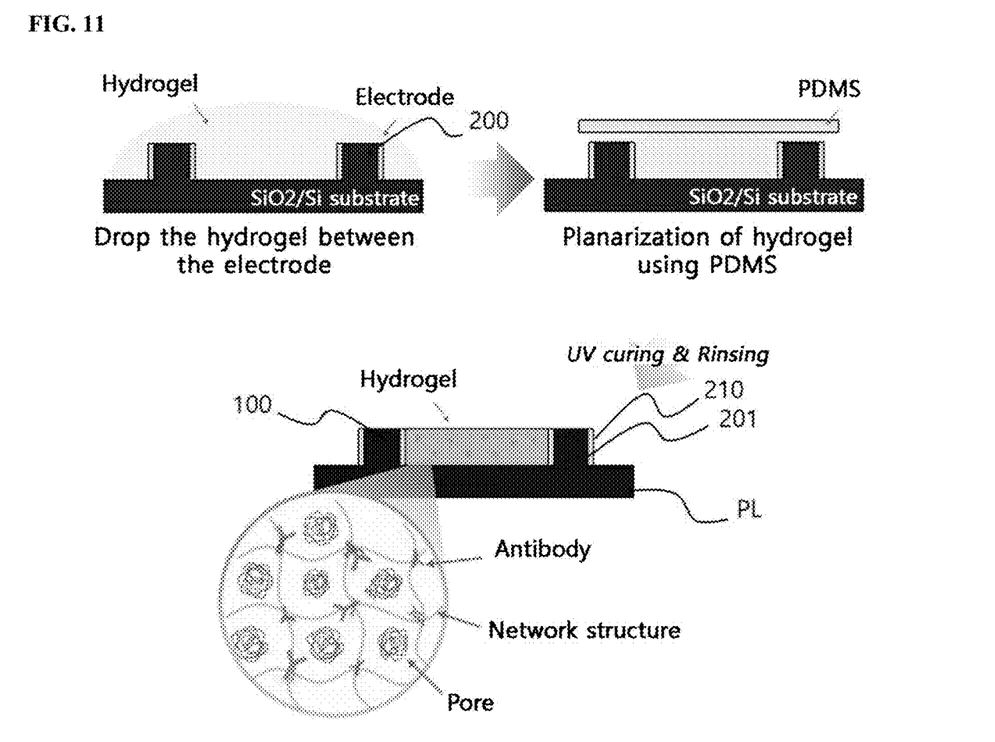
FIG. 11 is a diagram explaining a method for forming a hydrogel of the interdigitated microelectrode biosensor of FIG. 1.

FIG. 11 is a diagram explaining a method for forming a hydrogel of the interdigitated microelectrode biosensor of FIG. 1.

As shown in FIG. 11, first, a hydrogel 300 is applied so as to cover the entire region (including the first interdigitated microelectrode 100 and the second interdigitated microelectrode 200) of the interdigitated microelectrode biosensor.

Thereafter, the first interdigitated microelectrode 100 and the second interdigitated microelectrode 200 are covered with polydimethylsiloxane (PDMS) to planarize the hydrogel. Then, the PEGDA crosslinker is activated by UV curing to form a three-dimensional network structure. The PPEG porogen is removed by rinsing to form pores. That is, the size of the pores is determined by the PPEG porogen. The size of the pores can be controlled depending on the kind and proportion of the PEG porogen added.

Figure 12:
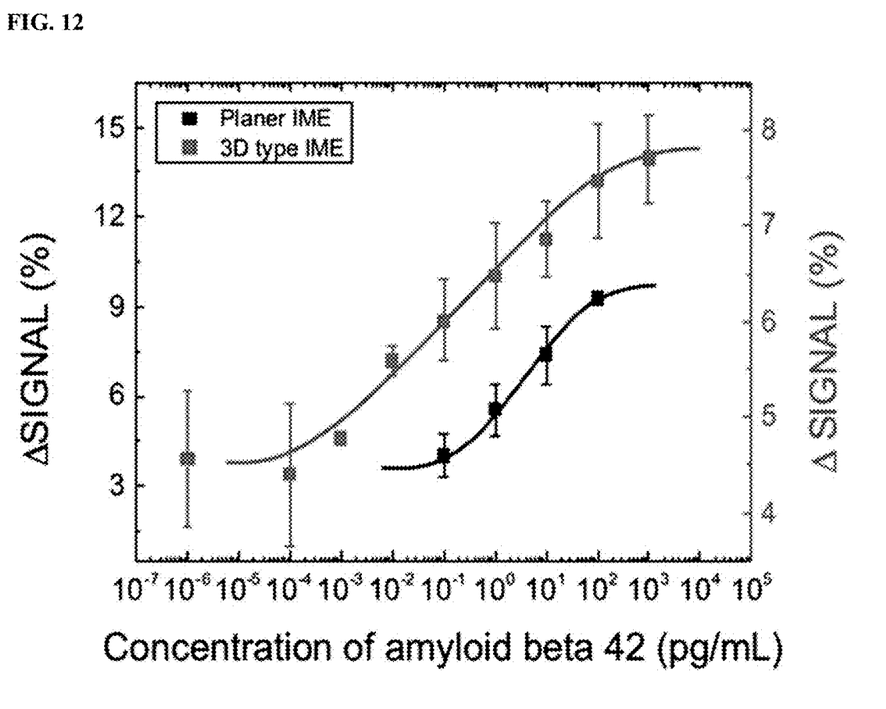
FIG. 12 is a graph showing a variation in the impedance detection efficiency of the hydrogel-based interdigitated microelectrode biosensor of FIG. 1.

FIG. 12 is a graph showing a variation in the impedance detection efficiency of the hydrogel-based interdigitated microelectrode biosensor of FIG. 1.

As shown FIG. 12, the formation of the hydrogel 300 between the first interdigitated microelectrode 100 and the second interdigitated microelectrode 200 results in a 100-fold increase in the limit of detection and an extended dynamic range compared to conventional biosensors in which no hydrogel is formed. These results are explained by an increased probability of reacting with an increased number of antibodies in the hydrogel 300 and sensitive detection of the reaction.

As is apparent from the foregoing, in the hydrogel-based interdigitated microelectrode biosensor of the present invention, the hydrogel 300 is provided between the interdigitated microelectrodes such that the presence and concentration of a biological substance, such as a protein, are detected by measuring the impedance between the interdigitated microelectrodes. This construction is effective in increasing the width and limit of impedance detection by tens to hundreds of times and improving the accuracy of impedance detection compared to conventional interdigitated microelectrode sensors.

In addition, the presence of size-controllable pores in the hydrogel 300 allows the detection of increased amounts of biological substances with high efficiency. This leads to an improvement in impedance detection limit, ensuring enhanced reliability and availability of the hydrogel-based interdigitated microelectrode biosensor.

While the present invention has been described in detail with reference to the embodiments thereof, those skilled in the art will appreciate that various changes and modifications can be made thereto without departing from the spirit and scope of the present invention as set forth in the appended claims.

What is claimed is:

1. A hydrogel-based interdigitated microelectrode biosensor comprising: a first interdigitated microelectrode having a plurality of first protrusion electrodes arranged in a comb-like shape on a substrate; a second interdigitated microelectrode facing the first interdigitated microelectrode and having a plurality of second protrusion electrodes arranged in a comb-like shape on the substrate, the second protrusion electrodes being arranged alternately with the first protrusion electrodes of the first interdigitated microelectrode; metal patterns formed to surround only both sides of the first and second interdigitated microelectrodes, respectively; and a hydrogel filled in a space between the first and the second interdigitated microelectrodes arranged alternately with each other.

2. The hydrogel-based interdigitated microelectrode biosensor according to claim 1, wherein the first interdigitated microelectrode and the second interdigitated microelectrode include: first and second interdigitated microelectrode patterns integrally formed with the substrate and made of the same material as the substrate.

3. The hydrogel-based interdigitated microelectrode biosensor according to claim 1, wherein the hydrogel comprises a polyethylene glycol diacrylate (PEGDA) crosslinker having a three-dimensional polymer network structure and a polyethylene glycol (PEG) porogen.

4. The hydrogel-based interdigitated microelectrode biosensor according to claim 1, wherein the hydrogel comprises a polyethylene glycol diacrylate (PEGDA) crosslinker having a three-dimensional polymer network structure and a polyethylene glycol (PEG) porogen; the PEGDA crosslinker is activated by exposure to UV light in a state in which the first and second interdigitated microelectrodes are covered with polydimethylsiloxane (PDMS), to form a three-dimensional network structure; and the size of the pores is controlled by varying the kind and proportion of the PEG porogen added and by rinsing off the PEG porogen.

* * * * *